US005749232A

United States Patent [19]

Sauer

[11] Patent Number: 5,749,232
[45] Date of Patent: May 12, 1998

[54] APPARATUS AND METHOD FOR PRODUCING AND INJECTING STERILE CRYOGENIC LIQUIDS

[75] Inventor: Richard A. Sauer, Hinsdale, Ill.

[73] Assignee: Air Liquide America Corporation, Houston, Tex.

[21] Appl. No.: 769,276

[22] Filed: Dec. 18, 1996

[51] Int. Cl.$^6$ ............................................ F17C 7/02
[52] U.S. Cl. .................... 62/50.1; 62/908; 422/28
[58] Field of Search .................. 62/50.1, 908; 422/28

[56] References Cited

U.S. PATENT DOCUMENTS

| | | | |
|---|---|---|---|
| 3,181,305 | 5/1965 | Schoenfelder | 62/908 |
| 3,415,069 | 12/1968 | Hauser . | |
| 3,500,652 | 3/1970 | Manns et al. | 62/908 |
| 3,866,428 | 2/1975 | Simonet et al. | 62/908 |
| 3,974,068 | 8/1976 | Ebner et al. . | |
| 4,150,548 | 4/1979 | Kemp et al. . | |
| 4,337,071 | 6/1982 | Yang . | |
| 4,431,545 | 2/1984 | Pall et al. . | |
| 4,620,962 | 11/1986 | Brodbeck . | |
| 4,717,406 | 1/1988 | Giacobbe . | |
| 4,759,848 | 7/1988 | Segura et al. . | |
| 5,122,175 | 6/1992 | Koyama et al. . | |
| 5,533,341 | 7/1996 | Schvester et al. . | |
| 5,548,962 | 8/1996 | Luger et al. | 62/908 |
| 5,557,924 | 9/1996 | Blanton et al. . | |

FOREIGN PATENT DOCUMENTS 3 342 440   6/1985   Germany .

WO 96/09510   3/1996   WIPO .

OTHER PUBLICATIONS

"Chem–Line II PF Disposable Filters", Chemical Products.
"BM Series Bellows Metering and Regulating Valves", NUPRO.
"DS Series Diaphragm Valves", NUPRO.
"Membralox ceramic gas filters", U.S. Filter.

*Primary Examiner*—Ronald C. Capossela
*Attorney, Agent, or Firm*—Burns, Doane, Swecker & Mathis, L.L.P.

[57] ABSTRACT

An apparatus for producing a sterile cryogenic liquid (for example into a container of food) is provided, as well as a method of use of same using a just-in-time approach to production. The apparatus includes at least one cryogenic liquid filter, the filter including filter media having the capability to effectively sterilize cryogenic liquids, the filter media positioned within a housing to accept non-sterile cryogenic liquid and produce sterile cryogenic liquid. The apparatus further includes at least one sterile cryogenic liquid receptor tube, the sterile cryogenic liquid receptor tube having a sterile cryogenic liquid outlet for outflowing sterile cryogenic liquid. The receptor tube is surrounded by a manifold which collects and drains spent condensed steam after a periodic filter sterilization cycle. The receptor tube also collects raw cryogenic fluid, which helps insulate sterile cryogen in the receptor tube. The cryogenic liquid filter is provided within a vacuum jacketed tank. A sheath is positioned over the cryogenic liquid filter within the tank for sterilizing the filter.

26 Claims, 6 Drawing Sheets

APPARATUS AND METHOD FOR PRODUCING AND INJECTING STERILE CRYOGENIC LIQUIDS

FIELD OF THE INVENTION

The present invention relates generally to cryogenic liquids and gases. In particular the present invention relates to the production and injection of a sterile cryogenic liquid in a manner which safeguards the sterility of the cryogenic liquid until it is dispensed.

RELATED ART

Cryogenic liquids and gases of high purity, such as nitrogen, helium, argon and the like, are preferred for a variety of industries. The semiconductor industry, for example, prefers ever increasingly purer nitrogen as a carrier gas for reactive species in the production of semiconductors.

Another industry desiring high purity inert gases is the food packaging industry, more particularly the canned food industry. Aluminum cans are being increasingly used in retail sales of soft drinks, fruit juices, coffee beverages, and the like. Aluminum cans, which can be made in two pieces, are often less expensive to produce than competing three piece cans. However, aluminum cans often do not have the compressive strength of steel cans, making the stacking of aluminum-canned food higher than a minimal height very difficult: the cans at the bottom of the stack are likely to fail. This is of course undesirable for a variety of reasons. Failure of cans could cause the food or beverage to leak from the can, causing slip-and-fall hazards for workers or store customers, and the spillage of food is often aesthetically distasteful, or because of foul smell. Therefore, if aluminum cans are to be used, it is desirous to use cryogenic liquids in droplet form dispensed into the can just before and/or during the sealing procedure. The cryogenic liquid vaporizes via heat transfer from the surroundings, and expands and thus pressurizes the can.

A problem that still presents itself to the user of cryogenic liquids is the fact that the bulk cryogenic liquid supply is not sterile. It has been found that liquid nitrogen contains between zero and three hundred viable microbes per liter of liquid cryogen. These microbes, if used in aseptic service, could act to spoil food products within a container.

The use of inert, sterile cryogenic liquids in aluminum canning is known, and methods and apparatus are described in U.S. Pat. Nos. 4,620,962 and 4,759,848. The '962 patent is directed to a method and apparatus to make sterile cryogenic liquid, wherein the cryogenic liquid to be sterilized is first vaporized, then sterilized as a gas and finally reliquified to provide sterile cryogenic liquid. Vaporization is carried out in a heat exchanger which is also used to cool the sterilized gas. The '848 patent discloses a method and an apparatus to sterilize a cryogenic liquid, wherein the unsterilized cryogenic liquid is provided in liquid (saturated) state to a microporous filter submerged in a subcooling cryogenic liquid having a temperature cooler than the saturated stream, the cryogenic liquid being thus sterilized and subcooled. The purpose of subcooling is to prevent the formation of gas bubbles in the saturated stream and, therefore, assures that the saturated liquid can pass quickly through the pores of the filter. These methods and apparatus, while producing sterile cryogenic liquids and gases, do not disclose or suggest means for maintaining the sterility of the sterile cryogenic liquid during dispensing.

Even if a supply of sterile nitrogen were available, in many instances a metering device, such as a needle valve or metering pump, is used to dispense the sterile liquid. These metering devices typically have very small outlet nozzles which can easily become clogged with ice formed from water vapor in the surrounding air as the drops of liquid cryogen are dispensed into the product. Ambient air is, of course, not sterile, and thus contamination of the food or semiconductor or other product is an acute problem. It is of course possible in theory to provide a "clean room" for the dispensing area, where the atmosphere is sterile, but this may be cost prohibitive when large food canning lines or other production lines are involved.

A sterile supply of a cryogenic liquid, such as liquid nitrogen, may be produced either by preventing living microbes from entering a sterile product via the use of a barrier or by killing the microbes within the cryogenic liquid. Killing the microbes in the bulk supply could be achieved using energy intensive means, such as heat, radiation, microwave, etc.; these techniques can, however, convert some or all of the liquid to a gas which would have to be reliquified for use in a cryogenic application. This approach would be very energy intensive and impractical. Therefore, the better alternative appears to be the use of a barrier or filtration device to keep the living microorganisms from entering the sterile product stream.

The production and dispensing of a sterile cryogenic liquid is disclosed in U.S. Pat. No. 5,533,341 ("the '341 patent") which issued on Jul. 9, 1996, incorporated by reference herein. In the '341 patent, and described in FIGS. 1–4 herein, is one method and apparatus for producing and dispensing sterile cryogenic liquids.

Figure 1:
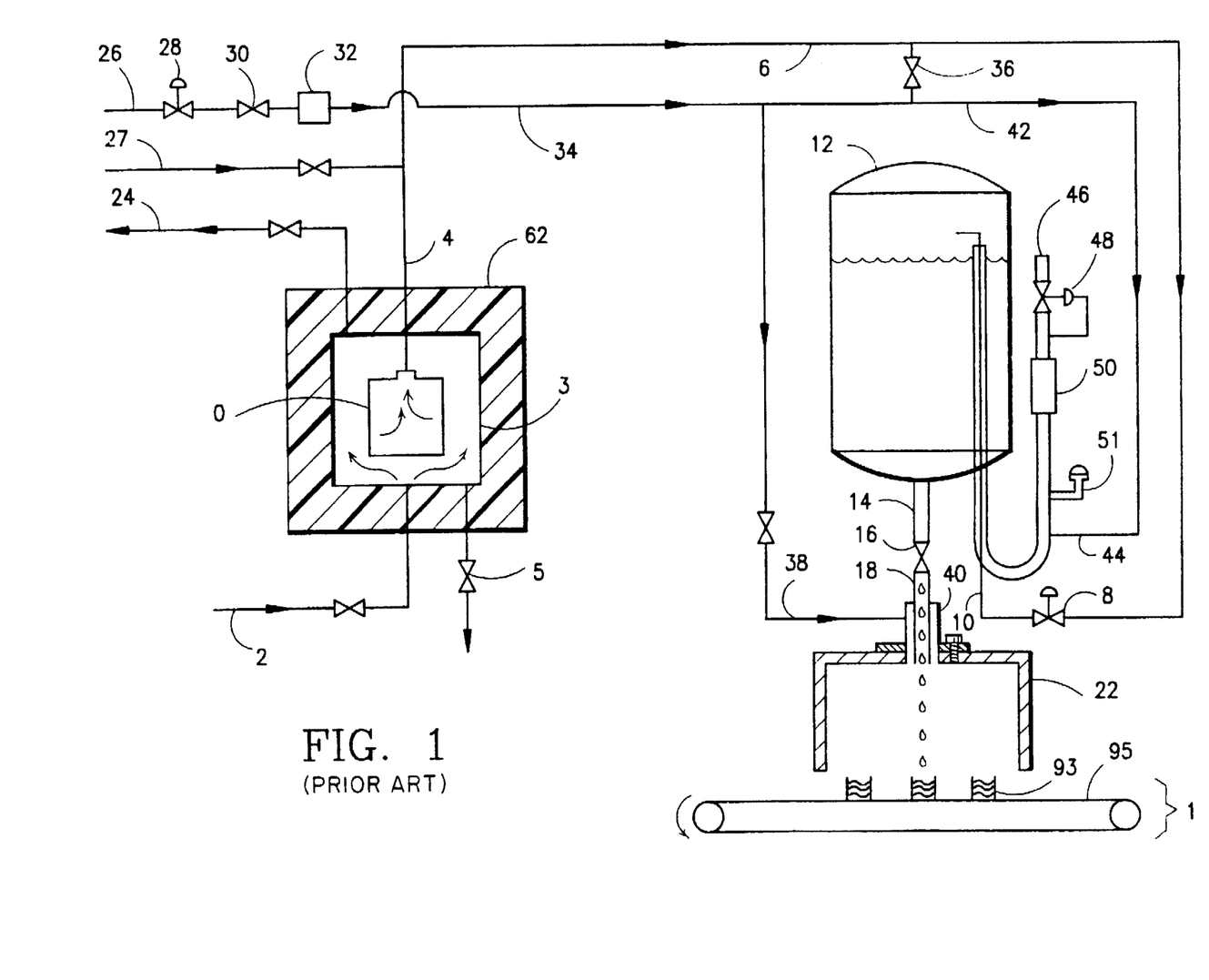
FIG. 1 is a schematic view (reduced) of an apparatus in accordance with U.S. Pat. No. 5,533,341 (prior art)

Referring to FIG. 1, non-sterile ("raw") liquid cryogen enters the apparatus via a conduit 2, passes through a liquid cryogen filter 3, and exits as sterile liquid cryogen via a conduit 4. Conduit 4 directs sterile liquid cryogen into a sterile liquid cryogen accumulator 12. At the lower end of accumulator 12 is a sterile liquid cryogen dispensing arrangement which includes a sterile cryogenic liquid accumulator outlet conduit 14, a sterile cryogenic liquid metering valve 16, the latter producing drops of liquid cryogen which pass through conduit 18 and on into a customer's aseptic packaging container 93. Cryogenic liquid filter 3 includes filter media 60.

Raw cryogenic gas enters the system through conduit 26 and a microporous cryogenic gas filter 32. Sterile cryogenic gas passes through conduit 38 to sheath 40 to provide a purge stream of sterile gaseous cryogen around the flow of sterile liquid cryogen from accumulator outlet conduit 18. The intent of the pressurization and purging with sterile gas is to maintain the liquid in a sterile condition.

A conduit 27 is connected to the filter 3 to allow a regeneration material, typically steam, to enter the apparatus to kill microbes which have been filtered out of the non-sterile cryogenic liquid and gas.

Figure 2:
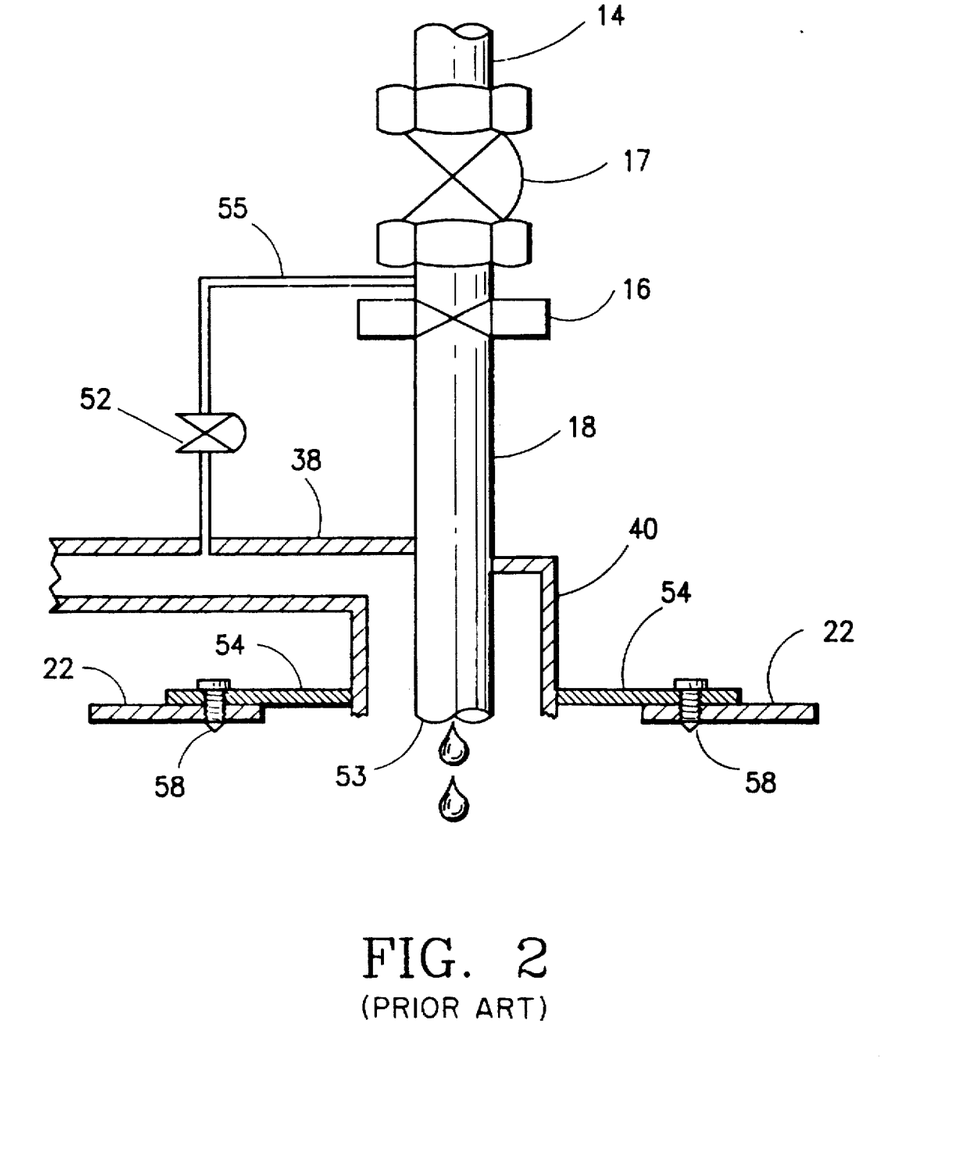
FIG. 2 is a schematic view (enlarged) of a sterile liquid cryogen injection component in accordance with U.S. Pat. No. 5,533,341 (prior art)

The provision of sterile cryogenic gas through conduit 38 and sheath 40 ensures the sterility of the sterile cryogenic liquid as it is being dispensed. The sterile gaseous cryogen is used to flush the tip of the nozzle at all times and to prevent freeze-up of the metering valve 16 during a process interruption.

Figure 3:
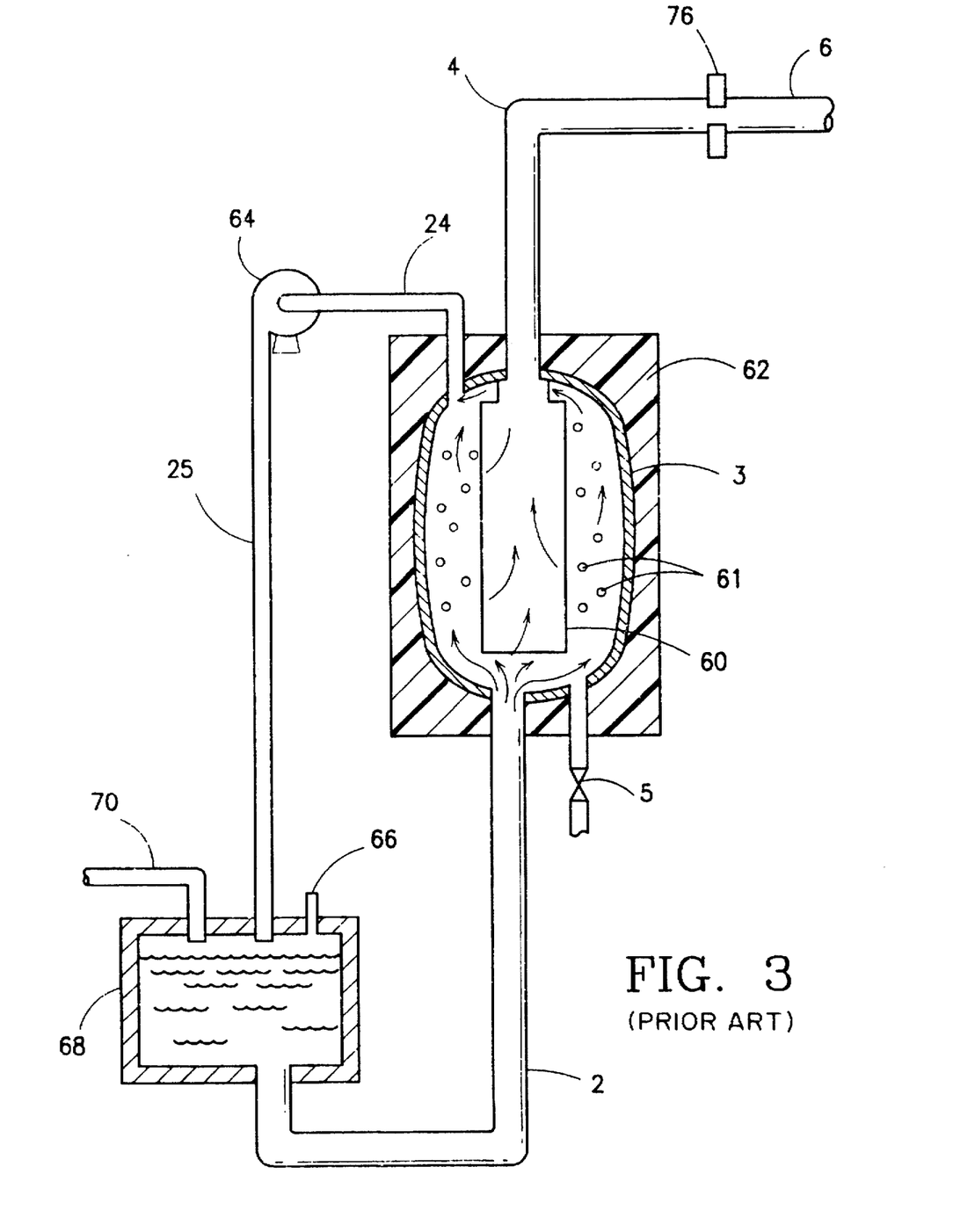
FIG. 3 is a schematic view (reduced) of a liquid cryogen filter and associated piping useful in the apparatus and method of U.S. Pat. No. 5,533,341 (prior art)

Referring to FIG. 3, raw cryogenic liquid enters filter housing 3 through conduit 2 and sterile cryogenic liquid leaves via conduit 4. Bubbles 61 form in housing 3 and exit filter housing 3 to the surroundings.

Figure 4:
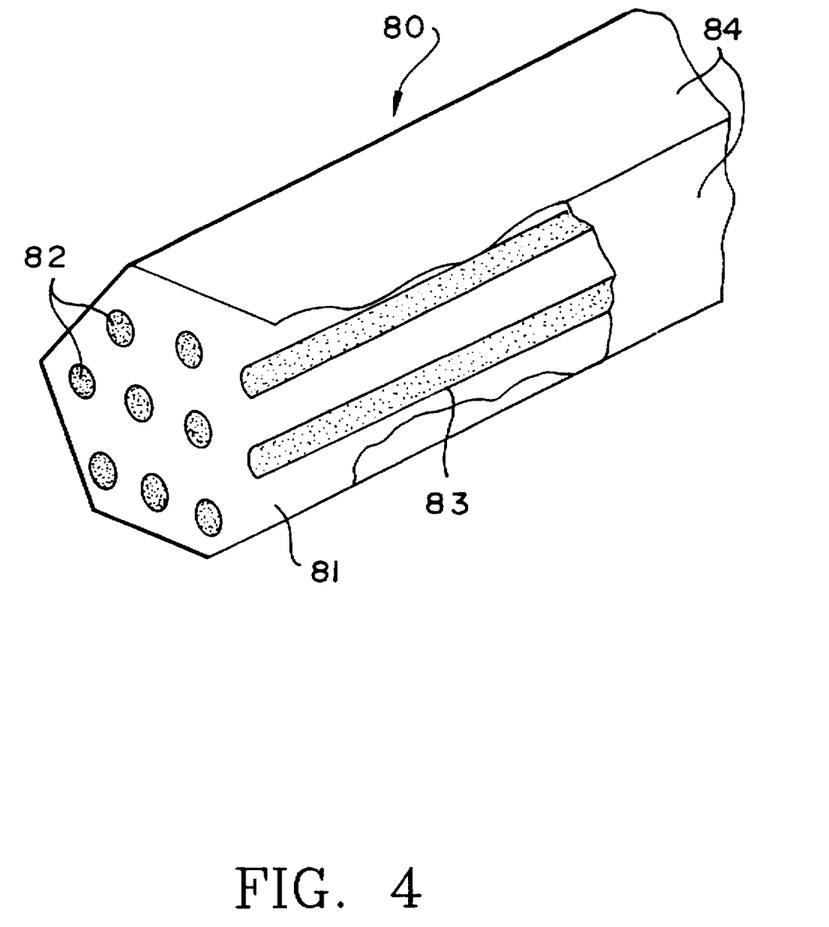
FIG. 4 is a perspective view of a ceramic filter media useful in the present invention.

A filter media 80 usable as filter media 60 (see FIG. 1) is illustrated perspectively in FIG. 4. Filter media 80 comprises a high purity, sintered ceramic material with a precisely calibrated pore size. The ceramic material comprises a multichannel support element 81 having a plurality of channels 82. Support element 81 is typically alumina having a microporous structure which is at the same time highly permeable and very strong, allowing operation under elevated temperature and pressure. Several layers of microporous ceramic material 83 are deposited in each channel 82.

The system and method described in the '341 patent, while overcoming many obstacles of previous systems, still does not provide "just-in-time", i.e., only as needed, inventories of sterile cryogenic liquids. Instead, the system and method described in the '341 patent are more suited for the production for sterile cryogenic liquids to be inventoried or stored. There is still, therefore, an unmet need for a just-in-time method and apparatus which simply and efficiently produces sterile cryogenic liquids from the bulk raw supply, ensures the sterility of the cryogenic liquid, and manages the injection of the sterile liquid cryogen into the product, e.g., food products, under canning line conditions and in other areas where portable sterile cryogenic liquid supplies are needed.

SUMMARY OF THE INVENTION

The present invention overcomes many deficiencies of previous systems in providing good quality sterile liquid cryogens using a just-in-time philosophy. The high quality of the cryogenic liquids produced by the method and apparatus of the invention is maintained by use of a sterile cryogenic gas purging system to pressurize the apparatus and create a sterile zone which essentially prevents contact of the sterile cryogenic liquid with non-sterile atmospheres. The present invention also has the benefit of providing for systems and methods which are less complex than prior systems and methods. Accordingly, the use of systems and methods of the present invention is more economical, because they are less costly to build and maintain, and provide the further benefit of allowing fewer possibilities for contamination by microbe ingress into the system.

As used herein, the terms cryogenic liquid and cryogenic gas refer to single component or compositions comprising more than one of argon, nitrogen, helium, krypton, nitrous oxide and the like. Further, a cryogenic liquid is saturated, and not subcooled, although a de minimis amount of subcooling may actually occur. Although all piping is preferably vacuum jacketed, it is contemplated that heat transfer from the atmosphere will substantially prevent subcooling in most if not all embodiments, and thus the presence of gas phase in the system is to be expected.

The term "just-in-time" means the generation of sterile cryogenic liquid from raw cryogenic liquid only as it is needed, i.e., just in time for use in a customer's product. A just-in-time approach to the generation of sterile cryogenic liquid greatly reduces the potential for microbes to enter the sterile cryogenic liquid, and also greatly reduces the complexity of operating and maintaining a sterile cryogenic liquid generation and delivery system. Thus, a just-in-time approach greatly minimizes the cost of generating and delivering sterile cryogenic liquid to a customer's product.

In accordance with one aspect of the present invention, an apparatus for producing and injecting a sterile cryogenic liquid is described, the apparatus comprising:

(a) a tank having insulation means, the tank adapted to contain a cryogenic liquid;

(b) a cryogenic liquid filter positioned within the insulated tank;

(c) a sheath positioned over a portion of the cryogenic liquid filter and connected to a supply of sterilization fluid for sterilizing the filter; and (d) a sterile cryogenic liquid outlet for dispensing sterile cryogenic liquid which has been filtered by the cryogenic liquid filter.

According to a preferred embodiment of the invention, the cryogenic filter is an elongated ceramic membrane filter having a plurality of channels formed along the length of the filter. The filter is preferably able to remove microbes having a size greater than 0.45 micrometer, more preferably greater than 0.2 micrometer. According to another aspect of the invention, a receptor tube is connected to a lower edge of the cryogenic liquid filter for receiving the sterile cryogenic liquid. The receptor tube extends out of the vacuum jacketed tank and is connected to the dispensing apparatus. The receptor tube is surrounded by a manifold which receives cryogenic liquid from the tank and helps to insulate the sterile cryogenic liquid within the receptor tube.

According to another aspect of the present invention, an apparatus for producing a sterile cryogenic liquid, comprises:

(a) a tank having insulation means, the tank adapted to contain a cryogenic liquid and adapted to be pressurized, the tank having a tank outlet;

(b) a cryogenic liquid filter positioned within the vacuum jacketed tank, the filter formed of a porous material for retaining microbes from the cryogenic liquid, and including a sterile cryogenic liquid outlet which is connected to the tank outlet; and (c) a sheath surrounding the cryogenic liquid filter for supplying a sterilization fluid to the filter to periodically sterilize the filter.

According to a further aspect of the present invention, a method of producing and dispensing a sterile cryogenic liquid includes the steps of:

(a) providing a non-sterile cryogenic liquid in an insulated tank, the liquid comprising at least submicron microbes;

(b) providing a filter within the vacuum vessel;

(c) passing the non-sterile cryogenic liquid through the filter within the vacuum vessel to produce sterile cryogenic liquid; and (d) dispensing the sterile cryogenic liquid which has been sterilized by the filter.

It will be understood that the method steps may be performed simultaneously in a continuous operation, or the liquid filter may operate for a time to produce a batch of sterile liquid cryogen for use in a particular application, after which the liquid flow to the liquid filter is interrupted and the dispensing step commenced. Many variations will become apparent to those skilled in the art.

The invention will be more fully understood with reference to the following detailed description of the invention and drawing figures.

BRIEF DESCRIPTION OF THE DRAWINGS

The figures are not to scale and are merely illustrative of the invention.

DESCRIPTION OF PREFERRED EMBODIMENTS

The components of preferred apparatus embodiments of the invention will now be described in detail, component by component, as well as preferred method embodiments.

Figure 5:
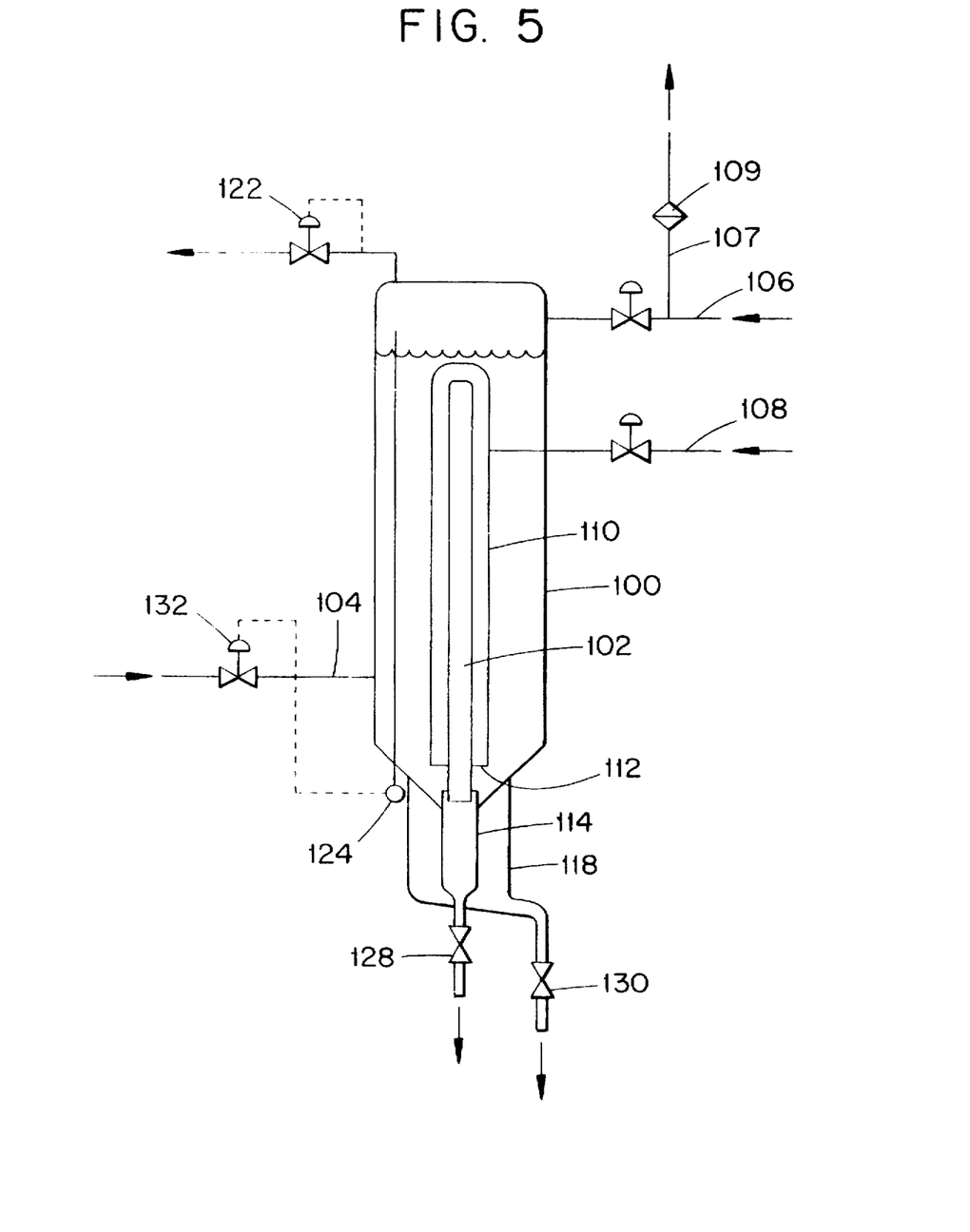
FIG. 5 is a schematic view of one embodiment of a liquid cryogenic filter apparatus of the present invention.
Figure 6:
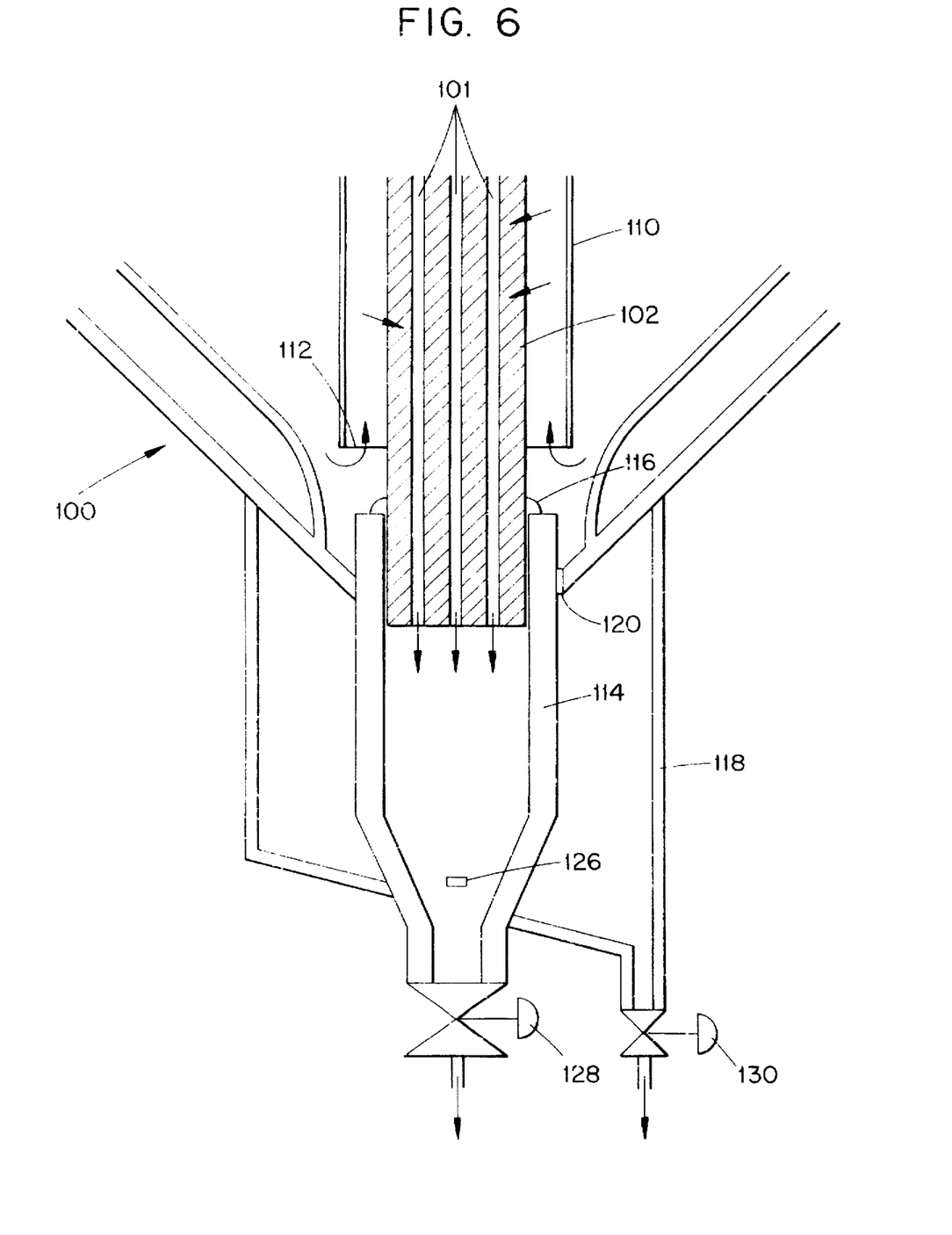
FIG. 6 is an enlarge schematic view of the bottom of the filter apparatus illustrated in FIG. 5.

An illustrative embodiment of the filtration system according to the present invention for producing sterile cryogenic liquid is illustrated in FIGS. 5 and 6. The system of FIGS. 5 and 6 uses a just-in-time approach to production of cryogenic liquid and minimizes the complexity of the apparatus so as to reduce the probability of microbes ingress into the sterile cryogenic liquid. The approach of the system of FIGS. 5 and 6 eliminates the accumulator 12 of the '341 patent, which is illustrated in FIG. 1, and instead delivers the sterile cryogenic liquid directly to the sterile cryogen injection system, thus providing direct communication with the injection system and preventing microbes from entering into the sterile cryogenic liquid.

The filtration system illustrated in FIG. 5 includes an insulated cryogenic liquid storage tank 100 having a preferably elongated, rod-shaped filter 102 positioned within the tank. Tank 100 is preferably vertical, preferably vacuum jacketed, and is connected to a first line 104 for supplying raw cryogenic liquid, a second line 106 for supplying gaseous cryogen, and a third line 108 for supplying steam or other sterilization means, such as alcohol. Each of these lines 104, 106, 108 is provided with a valve for controlling fluid delivery to tank 100. Line 106 also preferably includes a line 107 connecting to line 106 upstream of the valve on line 106. Line 107 includes a microporous cryogenic gas filter 109 which filters out microbes in the raw cryogenic gas in line 107. Filtered cryogenic gas from filter 109 may then be used in the system illustrated in FIGS. 1 and 2 in conduit 38.

It is conceivable that other liquid and/or gaseous compositions may be useful for the killing of the microbes. For example, sterilized and heated gases such as air, nitrogen, carbon dioxide, ethylene oxide, and the like may be used, depending on the availability of each. Further, it may be possible to use sterile liquids, such as hydrogen peroxide, and the like. Essentially any material that will kill microbes such as *pseudomonas diminutia* and the like may be employed.

Filter 102 is preferably a ceramic membrane filter, such as those described above with respect to FIGS. 3 and 4, which acts as a barrier to microbes in the cryogenic liquid supply within storage tank 100. Filter media useful for filter 102 are the ceramic filter media available under the trade designations MEMBRALOX or STERILOX, which are available from SCT, Tarbes, France, a subsidiary of U.S. Filter Co., of Pittsburgh, Pa.

While the ceramic filter media just described is preferred for sterilization of liquid cryogens, they may also be employed in sterilization of gaseous cryogens. Another preferred filter media, for both liquid and gaseous cryogen sterilization, are the filters known under the trade designation CHEM-LINE II PF, available from Millipore Co., Bedford, Mass. These filters comprise a plurality of polytetrafluoroethylene (PTFE) discs stacked upon each other and housed in a PTFE housing. This construction allows a wide range of operating temperatures because of the similarity of the housing and disc materials. The filtration area for the CHEM-LINE II PF-40 filter is about 3350 $cm^2$, and for the 0.1 micrometer model has a flow rate of about 15 liters/min at a pressure differential of 8 psi. For the PF-80 model, the area is about 6700 $cm^2$, and for the 0.1 micrometer model has a flow rate of about 25 liters/min at a pressure differential of 8 psi. Both models have a maximum operating temperature of about 300° F. (149° C.). Other preferred filter media include microporous glass and metal filters.

The filter media and housings (as well as the conduits, the receptor tube and manifold, the valves, and associated mechanical equipment) useful in the invention preferably withstand temperatures ranging from –320° F. to about 300° F. (–196° C. to about 150° C.). In addition, all devices and connections must be suitable for aseptic service.

Filter 102 is preferably mounted vertically inside tank 100 and includes a plurality of substantially vertical channels 101 as shown in the enlarged view of FIG. 6. Filter 102 may include, for example, 15–25 channels having diameters ranging from 1 to 10 mm. The channels may be square, circular, oval, rectangular, etc., with the same or different diameters. An upper end of filter 102 is closed off to prevent entry of the raw cryogenic liquid or gas which contains microbes into channels 101. Cryogenic liquid from tank 100 diffuses through the pores in filter 102 and sterile cryogenic liquid is discharged from the bottom of channels 101 in filter 102.

Filter 102 is surrounded by a sheath 110 which is positioned over the filter to direct the flow of steam from steam injection line 108 for sterilization of the filter. Sheath 110 has an open lower end 112 which allows the cryogenic liquid within tank 100 to pass into the sheath and through filter 102.

The bottom end of filter 102 is fitted into a receptor tube 114 which receives the sterile cryogenic liquid and delivers the sterile cryogenic liquid to a sterile injection system such as that illustrated in FIG. 2 through a valve 128. The bottom end of filter 102 is sealed within receptor tube 114 by a seal 116 which is illustrated in FIG. 6. Seal 116 may be made of elastomer or PTFE gaskets, 0 -rings, silicone caulk, a flex-washer, or other equivalent sealing material. Receptor tube 114 is mounted within the bottom of vacuum jacketed tank 100 with a connection between the receptor tube and the tank being welded, compression fitted, or provided with an equivalent connection.

A condensate collection manifold 118 is located beneath tank 100 and encloses a bottom portion of the tank and a majority of receptor tube 114. Condensate collection manifold 118 and tank 100 both have sloped lower walls to facilitate draining and blowing down of steam condensate after initial or periodic sterilization of the filter by steam injection.

Weep holes 120 are provided at the bottom of tank 100 which allow communication between the interior of the tank and the interior of the condensate collection manifold 118. Weep holes 120 allow for the draining of condensate after steam sterilization. In addition, weep holes 120 allow raw liquid cryogen to enter and fill condensate collection manifold 118 during cryogenic operation which insulates the sterilized liquid cryogen within the receptor tube 114 to prevent warming of the sterilized liquid cryogen.

Tank 100 is preferably provided with a back pressure regulator 122 which maintains a desired pressure within the tank independent of the liquid cryogen vaporization rate, fill rate, and withdrawal rate. In addition, the level of liquid cryogen within tank 100 is controlled by a level indicator 124, such as a capacitance probe, in combination with a valve 132. A thermocouple 126 is preferably provided within receptor tube 114 for sensing the temperature during sterilization as will be described below.

Receptor tube 114 is provided with a valve 128 for delivering sterilized liquid cryogen to a sterile injection system such as illustrated in FIG. 2. In addition, condensate collection manifold 118 is provided with a valve 130 for draining the condensate or remaining liquid cryogen from the collection manifold.

The filtration system illustrated in FIGS. 5 and 6 is useful both in a continuous process where liquid cryogen is continuously fed into and out of tank 100, and in a batch process in which the tank is filled with liquid cryogen and sterilized liquid cryogen is withdrawn as needed without refilling the tank. Moreover, the batch process would be useful in situations where a filter is placed directly in a raw liquid cryogen bulk storage tank or when a small portable vacuum jacketed pressure vessel is used, such as for on-the-spot medical applications.

The filtration system is generally sterilized prior to use and periodically during use by injecting sterilizing steam through steam injection line 108 into sheath 110. The steam is injected until the thermocouple 126 indicates that the desired sterilization temperature has been reached, for example 250° F. (121° C.). The sterilization is performed by continuing steam injection for at least 15 minutes, preferably at least 30 minutes after thermocouple 126 indicates that the desired sterilization is performed by The system is then purged with gaseous cryogen which is injected from gas injection line 106 while a back pressure of about 10 psig (170 kPa) is maintained by back pressure regulator 122. The steam condensate is then drained and blown-down through valves 128 and 130. After thoroughly drying the internal components of the system, tank 100 is filled with raw cryogenic liquid and valve 128 is opened to establish the desired flow rate of sterilized cryogenic liquid through the injection system of FIG. 2.

In terms of the food packaging industry, sterilization means the retention of microbes having a size of 0.45 micrometer or larger, more preferably 0.2 micrometer or larger. This degree of sterilization is probably the same for the medical industry for the supply of oxygen. In the semiconductor or microelectronics industry, sterilization may mean the retention of microbes and other particulate matter having a size greater than 0.1 micrometer. It is expected that the semiconductor industry will continue to demand even greater purity gases and liquids, so that these numbers are bound to change (decrease) with time. As used herein sterilization will take different meanings in accordance with the customer or end user's needs.

It is conceivable that, in certain embodiments, the sterile cryogen production systems of the '341 patent and the present invention could be piped together in parallel flow relationship, both supplying a sterile cryogen injection system as disclosed in said patent. Both systems would utilize a similar sterile liquid nitrogen injection system.

Various modifications and alterations of this invention will become apparent to those skilled in the art without departing from the scope thereof. It should be understood, therefore, that the scope of this invention is not to be limited to the illustrative embodiments set forth herein, but is to be determined by the limitations set forth in the claims and equivalents thereof.

What is claimed is:

1. An apparatus for producing a sterile cryogenic liquid, the apparatus comprising:
   (a) a tank having insulating means, the tank adapted to contain a raw cryogenic liquid;
   (b) a cryogenic liquid filter positioned within the tank to retain contaminants;
   (c) a sheath positioned over a portion of the cryogenic liquid filter and adapted to be connected to a supply of sterilization fluid for sterilizing the filter; and
   (d) a sterile cryogenic liquid outlet for outflowing sterile cryogenic liquid which has been filtered by the cryogenic liquid filter.

2. Apparatus in accordance with claim 1, wherein the cryogenic filter is selected from the group consisting of a ceramic membrane filter, a PTFE filter, a glass filter, and a metal filter.

3. Apparatus in accordance with claim 1, wherein the cryogenic filter includes at least one channel for dispensing sterile cryogenic liquid.

4. Apparatus in accordance with claim 1, wherein the cryogenic filter has an elongated shape and a plurality of channels formed along the length of the filter.

5. Apparatus in accordance with claim 1 wherein the cryogenic filter is able to retain microbes having a size greater than 0.45 micrometer.

6. Apparatus in accordance with claim 1 wherein the cryogenic filter is able to retain microbes having a size greater than 0.2 micrometer.

7. Apparatus in accordance with claim 1 wherein the sheath surrounds the cryogenic liquid filter and has an opening at a lower end.

8. Apparatus in accordance with claim 1 further comprising:
   a receptor tube connected to the sterile cryogenic liquid outlet for receiving the sterile cryogenic liquid, and
   a sterile dispensing apparatus which is adapted to substantially prevent contact of the sterile cryogenic liquid with a non-sterile atmosphere,
   the receptor tube extending out of the insulated tank and connected to the sterile dispensing apparatus.

9. Apparatus in accordance with claim 8, further comprising a manifold surrounding said receptor tube, said manifold being adapted to receive and drain spent sterilizing fluid and raw cryogenic liquid from the tank, said manifold helping to insulate the sterile cryogenic liquid within the receptor tube.

10. Apparatus in accordance with claim 1, wherein said insulation means is vacuum jacketing.

11. An apparatus for producing a sterile cryogenic liquid, the apparatus comprising:
   (a) a tank having insulation means, the tank adapted to contain a raw cryogenic liquid and adapted to be pressurized, said tank having a tank outlet;
   (b) a cryogenic liquid filter positioned within the insulated tank, the filter formed of a porous material for retaining microbes from the cryogenic liquid, and including a sterile cryogenic liquid outlet which is connected to the tank outlet; and
   (c) a sheath surrounding the cryogenic liquid filter for supplying a sterilization fluid to the filter to sterilize the filter.

12. Apparatus in accordance with claim 11, wherein the cryogenic filter is selected from the group consisting of a ceramic membrane filter, a PTFE filter, a glass filter, and a metal filter.

13. Apparatus in accordance with claim 11, wherein the cryogenic filter includes at least one channel for dispensing sterile cryogenic liquid.

14. Apparatus in accordance with claim 11, wherein the cryogenic filter has an elongated shape and a plurality of channels formed along the length of the filter.

15. Apparatus in accordance with claim 11, wherein the cryogenic filter is able to retain microbes having a size greater than 0.45 micrometer.

16. Apparatus in accordance with claim 11, wherein the cryogenic filter is able to retain microbes having a size greater than 0.2 micrometer.

17. Apparatus in accordance with claim 11, wherein the sheath surrounds the cryogenic liquid filter and has an opening at a lower end.

18. Apparatus in accordance with claim 11, further comprising:

a receptor tube connected to the sterile cryogenic liquid outlet for receiving the sterile cryogenic liquid, and a sterile dispensing apparatus which is adapted to substantially prevent contact of the sterile cryogenic liquid with a non-sterile atmosphere, the receptor tube extending out of the insulated tank and connected to the sterile dispensing apparatus.

19. Apparatus in accordance with claim 18, further comprising a manifold surrounding said receptor tube, said manifold being adapted to receive and drain spent sterilizing fluid and raw cryogenic liquid from the tank, said manifold helping to insulate the sterile cryogenic liquid within the receptor tube.

20. Apparatus in accordance with claim 11, wherein said insulation means vacuum jacketing.

21. A method of producing and dispensing a sterile cryogenic liquid, the method comprising the steps of:

(a) providing a non-sterile cryogenic liquid in an insulated tank, the liquid comprising at least submicron microbes;

(b) providing a filter within the insulated tank;

(c) passing the non-sterile cryogenic liquid through the filter within the insulated tank to produce a sterile cryogenic liquid by retaining said microbes on said filter; and (d) dispensing the sterile cryogenic liquid which has been sterilized by said filter via a sterile dispenser.

22. Method in accordance with claim 21, wherein the filter is initially and periodically sterilized by injecting a sterilization fluid into a sheath surrounding the filter.

23. Method in accordance with claim 21, wherein the sterilization fluid is steam.

24. Method in accordance with claim 21, wherein the non-sterile cryogenic liquid passes through a porous surface of the filter, which retains said microbes and passes sterile cryogenic fluid into a channel in the filter.

25. Method in accordance with claim 21, wherein said step of providing a filter further comprises a step of selecting a filter from the group consisting of a ceramic membrane filter, a PTFE filter, a glass filter, and a metal filter.

26. Method in accordance with claim 21, wherein said step of providing said insulated tank further comprises a step of providing a vacuum jacketed tank.

* * * * *